(12) United States Patent
Oney

(10) Patent No.: US 10,462,989 B2
(45) Date of Patent: Nov. 5, 2019

(54) SYSTEMS AND METHODS FOR CULTIVATING AND HARVESTING BLUE WATER BIOALGAE AND AQUACULTURE

(71) Applicant: Stephen K. Oney, Manassas, VA (US)

(72) Inventor: Stephen K. Oney, Manassas, VA (US)

( * ) Notice: Subject to any disclaimer, the term of this patent is extended or adjusted under 35 U.S.C. 154(b) by 302 days.

(21) Appl. No.: 14/203,761

(22) Filed: Mar. 11, 2014

(65) Prior Publication Data

US 2014/0259896 A1    Sep. 18, 2014

Related U.S. Application Data

(60) Provisional application No. 61/779,238, filed on Mar. 13, 2013.

(51) Int. Cl.
*A01G 33/00* (2006.01)
*C12N 1/12* (2006.01)

(52) U.S. Cl.
CPC ............ *A01G 33/00* (2013.01); *C12N 1/12* (2013.01); *Y02A 40/88* (2018.01); *Y02P 60/247* (2015.11)

(58) Field of Classification Search
CPC ....... A01G 33/00; A01D 44/00; C12M 27/02; C12M 27/06; C12M 27/10
USPC ........... 47/1.4; 119/208, 204, 213, 215, 224, 119/238; 435/3, 257.1, 286.5, 292.1, 435/294.1
See application file for complete search history.

(56) References Cited

U.S. PATENT DOCUMENTS

| | | | |
|---|---|---|---|
| 2,204,584 A * | 6/1940 | Flower | 119/235 |
| 2,699,135 A * | 1/1955 | Steiner | 114/73 |
| 3,248,812 A * | 5/1966 | Gardner | 37/314 |
| 3,440,146 A | 4/1969 | Louw | 203/11 |
| 3,467,013 A | 9/1969 | Conner | 417/244 |
| 3,468,762 A | 9/1969 | Klitzsch | 202/186 |
| 3,568,621 A * | 3/1971 | Kawasaki | B63B 35/70 114/248 |
| 3,841,254 A | 10/1974 | Dragonas | 114/77 |
| 3,928,145 A | 12/1975 | Othmer | 203/11 |

(Continued)

FOREIGN PATENT DOCUMENTS

DE    197 34 981 A1    6/1998
DE    102 11 788 A1    10/2003

(Continued)

OTHER PUBLICATIONS

International Search Report dated Aug. 21, 2014 of related International Patent Application No. PCT/US14/27659.

(Continued)

*Primary Examiner* — Tien Q Dinh
*Assistant Examiner* — Ebony E Evans
(74) *Attorney, Agent, or Firm* — Bradley Arant Boult Cummings LLP

(57) ABSTRACT

Methods and systems for utilizing deep ocean water in the cultivation and harvesting of nutrients and $CO_2$ for algae and other valuable aquaculture species for the production of algal biomass and the like. The systems of the present invention include a floating deep water harvesting barge, a containment device, and a storage or pumping device. The containment device may be a closed system, an open system, or a photo-bioreactor. The present invention is also directed to improved methods for drying algae biomass and further downstream applications and uses of the algae biomass.

12 Claims, 8 Drawing Sheets

(56) References Cited

U.S. PATENT DOCUMENTS

| | | | |
|---|---|---|---|
| 3,955,317 A * | 5/1976 | Gudin | C12M 21/02 435/292.1 |
| 4,036,028 A | 7/1977 | Mandrin | 62/52 |
| 4,052,800 A * | 10/1977 | Fuhrboter et al. | 37/314 |
| 4,078,975 A | 3/1978 | Spears, Jr. | 203/10 |
| 4,172,766 A | 10/1979 | Laing et al. | 202/173 |
| 4,233,153 A | 11/1980 | Hammel et al. | 203/10 |
| 4,261,160 A * | 4/1981 | Niewiera | 56/8 |
| 4,293,240 A | 10/1981 | Ogimoto et al. | 405/195 |
| 4,302,297 A | 11/1981 | Humiston | 202/185 R |
| 4,311,012 A | 1/1982 | Finley | 60/641.7 |
| 4,356,785 A | 11/1982 | Baile | 114/264 |
| 4,434,572 A * | 3/1984 | Sheldon et al. | 43/6.5 |
| 4,452,696 A | 6/1984 | Lopez | 210/170.11 |
| 4,545,862 A * | 10/1985 | Gore | B01D 61/364 159/DIG. 27 |
| 4,568,522 A | 2/1986 | Corbett | 422/186 |
| 4,618,421 A | 10/1986 | Kantor | 210/170.09 |
| 4,779,404 A * | 10/1988 | Bell | 56/9 |
| 4,966,713 A * | 10/1990 | Keys | C02F 1/5263 210/705 |
| 4,993,348 A | 2/1991 | Wald | 114/265 |
| 5,069,023 A * | 12/1991 | Prochaska et al. | 56/9 |
| 5,082,564 A * | 1/1992 | Halff | B01D 61/00 210/321.78 |
| 5,095,851 A * | 3/1992 | Bourg | A01K 61/00 114/36 |
| 5,197,263 A | 3/1993 | Midtling et al. | 56/8 |
| 5,229,005 A | 7/1993 | Fok et al. | 210/652 |
| 5,235,797 A * | 8/1993 | Sygen et al. | 56/9 |
| 5,306,397 A | 4/1994 | Schmidt | 203/11 |
| 5,527,456 A * | 6/1996 | Jensen | B01D 21/04 210/170.01 |
| 5,541,056 A * | 7/1996 | Huntley | C12M 21/02 435/257.1 |
| 5,582,691 A | 12/1996 | Flynn et al. | 203/11 |
| 5,840,159 A | 11/1998 | Rosenblad | 203/10 |
| 5,914,041 A | 6/1999 | Chancellor | 210/641 |
| 5,970,846 A | 10/1999 | Roehr | 99/276 |
| 6,158,220 A | 12/2000 | Hansen et al. | 60/649 |
| 6,223,669 B1 | 5/2001 | Bowden | 114/65 |
| 6,391,205 B1 * | 5/2002 | McGinnis | B01D 61/002 210/642 |
| 6,484,668 B2 * | 11/2002 | Riverin | A01K 80/00 119/201 |
| 6,694,910 B1 | 2/2004 | Sharapov | 114/264 |
| 7,153,423 B2 | 12/2006 | Gordon | 210/242.1 |
| 7,306,724 B2 | 12/2007 | Gordon | 210/241 |
| 7,416,643 B2 * | 8/2008 | Yonover | C02F 1/043 159/903 |
| 7,455,778 B2 | 11/2008 | Gordon | 210/652 |
| 7,510,658 B2 | 3/2009 | Gordon | 210/652 |
| 7,658,843 B2 | 2/2010 | Krock et al. | 210/170.11 |
| 7,743,733 B2 * | 6/2010 | Harrison | A01K 61/02 119/210 |
| 7,855,061 B2 * | 12/2010 | Vance | C12M 21/02 435/160 |
| 8,110,395 B2 * | 2/2012 | Lewnard | B01D 53/84 435/292.1 |
| 8,409,845 B2 * | 4/2013 | Trent | A01G 33/00 435/257.1 |
| 9,248,405 B2 * | 2/2016 | McGinnis | B01D 61/002 |
| 9,352,281 B2 * | 5/2016 | McGinnis | B01D 61/002 |
| 2003/0024803 A1 | 2/2003 | Max | 203/10 |
| 2004/0065614 A1 | 4/2004 | Gordon et al. | 210/650 |
| 2004/0084156 A1 | 5/2004 | Hata | 159/47.1 |
| 2004/0206681 A1 | 10/2004 | Gordon | 210/259 |
| 2005/0082214 A1 | 4/2005 | Max | 210/220 |
| 2006/0144789 A1 * | 7/2006 | Cath | B01D 61/002 210/641 |
| 2007/0039860 A1 | 2/2007 | Krock et al. | 210/170.01 |
| 2007/0048859 A1 * | 3/2007 | Sears | C12M 21/02 435/289.1 |
| 2008/0290032 A1 | 11/2008 | Ton That | 210/651 |
| 2009/0130706 A1 | 5/2009 | Berzin et al. | 435/41 |
| 2009/0250398 A1 | 10/2009 | Meller | 210/636 |
| 2009/0298159 A1 | 12/2009 | Wu et al. | 435/257.3 |
| 2010/0050502 A1 * | 3/2010 | Wu | C12N 1/12 44/308 |
| 2010/0105129 A1 * | 4/2010 | Sanchez-Pina | C12M 21/02 435/286.5 |
| 2010/0170149 A1 * | 7/2010 | Keeler | C12M 21/02 47/1.4 |
| 2010/0216203 A1 | 8/2010 | Trent et al. | 435/166 |
| 2011/0204279 A1 | 8/2011 | Minor et al. | 252/68 |
| 2012/0115210 A1 * | 5/2012 | Winters | C12M 21/02 435/257.1 |
| 2012/0180656 A1 * | 7/2012 | Jeong | B01D 61/002 95/45 |
| 2012/0235415 A1 | 9/2012 | Madison | 290/54 |
| 2015/0128838 A1 * | 5/2015 | Bryan | C12M 47/02 114/61.1 |

FOREIGN PATENT DOCUMENTS

| | | | |
|---|---|---|---|
| EP | 0009387 A1 | 4/1980 | |
| EP | 0 968 755 A | 1/2000 | |
| ES | 2 165 824 A1 | 3/2002 | |
| JP | 2000069877 A * | 3/2000 | |
| WO | WO 2005/068605 A1 | 7/2005 | |
| WO | WO 2010/059801 A2 * | 5/2010 | |
| WO | WO 2012/102849 A1 | 8/2012 | |
| WO | WO 2013071447 A1 * | 5/2013 | B63B 27/34 |

OTHER PUBLICATIONS

Lampe, H., et al., "PCS-Preussag Conversion System Mobile Floating Seawater Desalination Plant", Desalination 114, pp. 145-151, (1997).
U.S. Appl. No. 11/513,602, filed Aug. 2006.
U.S. Appl. No. 11/471,747, filed Jun. 2006.
International Search Report dated Jul. 1, 2014 of corresponding International Patent Application No. PCT/US14/23701.
International Search Report dated Jun. 27, 2014 of corresponding International Patent Application No. PCT/US14/23676.

* cited by examiner

SYSTEMS AND METHODS FOR CULTIVATING AND HARVESTING BLUE WATER BIOALGAE AND AQUACULTURE

CROSS-REFERENCE TO RELATED APPLICATIONS

This application claims priority to U.S. Provisional Patent Application No. 61/779,238, which was filed on Mar. 13, 2013, the entire disclosure of which is incorporated by reference herein.

FIELD OF THE INVENTION

The present invention is directed to large-scale algal biofuel and aquaculture development. In particular, the present invention is directed to systems and methods for the cultivation and harvesting of algal (aquaculture) in ways that remove the land requirements, nutrient sources/usage, carbon sequestration/sources, and energy balance concerns typically associated with large-scale implementation.

BACKGROUND OF THE INVENTION

Increasing energy access and energy security are both seen as key actions for reducing poverty thus contributing to the Millennium Development Goals. Access to modern energy services such as electricity or liquid fuels is a basic requirement to improve living standards. One of the steps taken to increase energy access and reduce fossil fuel dependency is the production of biofuels, especially because biofuels are currently the only short-term alternative to fossil fuels for transportation. However, despite the fact that first generation biofuels (i.e., land-based biofuels produced from agricultural feedstocks) can also be used as food or for feed purposes, the possible competition between food and fuel makes it impossible to produce enough first generation biofuel to offset a large percentage of the total fuel consumption for transportation.

Indeed, land-based biofuels are limited by available suitable agricultural acreage to support plant feedstock growth without direct competition with food feedstocks, rain forests, or other important land environments. Table 1 below shows the respective yields per hectare that can be expected for various commercially grown land-based biofuel crops.

TABLE 1

Typical oil yields from the various biomass sources in ascending order

| S.N. | Crop | Oil yield (l/ha) |
|---|---|---|
| 1 | Corn | 172 |
| 2 | Soybean | 446 |
| 3 | Peanut | 1,059 |
| 4 | Canola | 1,190 |
| 5 | Rapeseed | 1,190 |
| 6 | Jatropha | 1,892 |
| 7 | Karanj (*Pongamia pinnata*) | 2,590 |
| 8 | Coconut | 2,689 |
| 9 | Oil palm | 5,950 |
| 10 | Microalgae (70% oil by wt.) | 136,900 |
| 11 | Microalgae (30% oil by wt.) | 58,700 |

Source: Chisti [2007]; Lele [http://www.svlele.com/karanj.htm]; http://journeytoforever.org/biodiesel_yield.html Table 1 also shows the high yield per hectare for microalgae. In fact, microalgae represents orders of magnitude higher production per hectare potential over land-based biomass crops currently used for biofuel production. Thus, in recent years, biofuel production from algae has been a focused attraction as a possible alternative to fossil fuel consumption and its alternative land-based biofuel production. Algae have a number of characteristics that allow for production concepts that are significantly more sustainable than their fossil fuel and land-based biofuel alternatives. These include, but are not limited to, high biomass productivity, an almost 100 percent fertilizers (nutrients required for growth) use efficiency, and the possibility of utilizing marginal, infertile land, salt water, waste streams as a nutrient supply and combustion gas source to generate a wide range of fuel and non-fuel products.

For example, algae are very efficient at converting light, water, and carbon dioxide ($CO_2$) into biomass in a system that does not necessarily require agricultural land. In fact, depending on the concept, the water can be salty and the nutrients can come from waste streams. Depending on the species and cultivation conditions, algae can contain extremely high percentages of lipids or carbohydrates that are easily converted into a whole range of biofuels including biodiesel or bioethanol. In addition, the remaining biomass may be used in a number of non-fuel applications including those in the chemical, agricultural, and paper industries. Furthermore, another competitive advantage of algal biofuels is that their development can make use of current fossil fuel infrastructures. Thus, algae-based products can serve as an alternative to a wide range of products that are currently produced from fossil resources or land-based agriculture without requiring high quality land and, in some cases, without requiring fresh water, with $CO_2$ as the only carbon input.

In spite of this potential, in December 2012, a review committee of the National Academy of Sciences (NAS) concluded that the scale-up of algal biofuel production sufficient to meet at least five percent of the United States demand for transportation fuels, which was 784 billion liters in 2010, would place unsustainable demands on energy, water, and nutrients with current technologies and knowledge. The NAS report had several categories of concern with respect to the potential sustainability concerns for large-scale development of algal biofuels. The most serious concerns include (1) the quantity of water (fresh water or saline water) required for algae cultivation and the quantity of freshwater addition and water purge to maintain the appropriate water chemistry, especially in open-pond systems and arid regions, (2) supply of the key nutrients for algal growth—nitrogen, phosphorus, and $CO_2$, (3) appropriate land area with suitable climate and slope, (4) energy return on investment, and (5) GHG emissions over the life cycle of algal biofuels. Other less pressing concerns discussed in the NAS report include, but are not limited to, the presence of waterborne toxicants in cultivation systems that use flue gas as a source of $CO_2$ or wastewater as a source of culture water and nutrients, particularly if fertilizers or feedstuff are to be produced as co-products, the effects from land-use changes if pasture and rangeland are to be converted to algae cultivation, the air-quality emissions over the life cycle of algal biofuels, the potential effects on local climate, the potential alteration of species composition in receiving waters, the effects on terrestrial biodiversity, waste products, and the potential presence of pathogens if wastewater is used for cultivation. Similar issues exist with regard to aquaculture in general when considering long-term sustainability.

Given that the agricultural demand for water in the United States and many areas of the world account for 85 percent or more of consumptive water use, large-scale production of biomass, including algae, has the potential for large regional strain on water systems unless non-freshwater sources are used when possible. The freshwater demands of algal biofuel production will be high if algal biofuels are used to substitute for a significant fraction of annual U.S. liquid transportation fuel consumption, particularly if open ponds are to be used for algae cultivation. If open ponds are used for algae production, as is current "state-of-the-art" technologies, then a significant amount of water will be required to replace evaporative losses from the pond surface and to prevent dissolved salt and silt buildup in biomass cultivation systems. Recent estimates reported by the US Department of Energy suggest that water losses on the order of several hundred liters of water per liter of algal oil or algal biodiesel produced would result from operation of open ponds in arid, sunny regions of the continental United States. Cost effective approaches for reducing evaporative water loss and for dealing with salinity build-up need to be developed. Such approaches will be more important for inland sites where evaporation and salinity build-up are expected to be higher than in coastal marine operational settings that have relatively high humidity. If the algal biofuel industry relies heavily on freshwater resources, it could face a considerable setback as the increased use of freshwater resources becomes less acceptable to the public. Therefore, water recycling and/or use of non-freshwater resources are important to ensuring the social acceptability of the large water requirements for algal biofuel production.

Algae require key elemental nutrients for metabolic maintenance and growth. Photoautotrophic algae use photosynthesis to convert light energy into new algal biomass with an elemental stoichiometry that on average obeys the following equation $$106CO_2 + 16NO_3^- + HPO_4^{2-} + 122H_2O + 18H^+ \leftrightarrow C_{106}H_{263}O_{110}N_{16}P + 138O_2$$

The elemental content of algae can be expressed more simply as $$(CH_2O)106(NH_3)16(H_3PO_4)$$

These equations provide a basis for quantitative predictions to be made about the carbon, nitrogen and phosphorous demands of algal biomass production. Providing sufficient and stable supplies of $CO_2$, nitrogen, and phosphorous is essential if algal biofuel production is to be deployed at a commercial scale.

The estimated nutrient requirements for algal biofuel production are substantial. Current estimates suggest that 14-35 kilograms of $CO_2$ is required to produce 1 gallon of algal oil or biodiesel. Additional estimates suggest a nutrient requirement of approximately 0.61 kg N and 0.083 kg P per gallon of algal oil or biodiesel for a 50% oil content algal biomass. If nutrients are not recycled or supplied from waste sources under current cultivation technologies, nutrient requirements of algae for fuels could incur indirect and unintentional impacts on food prices through direct competition for limited fertilizer resources. It will additionally prove detrimental to the algal biofuel industry if it is viewed as a massive sink for nutrients that are in short supply, particularly if it is perceived that they are in direct competition with food producers.

Another major constraint on the future expansion of biofuel production is likely to be the limited amount of land suitable for producing bioenergy crops. The sites where algal cultivation systems can be installed will be constrained by high land cost, agricultural activity, environmental value, and intrinsic cultural value of the land being considered. The diverse set of site-specific factors would have to be carefully matched to the cultivation systems used for algal biofuel production if the essential requirements for successful large-scale algal biomass production (suitable land and climate, sustainable water supplies, and sustainable nutrient supplies) are to be aligned in terms of their geographical location. Meeting all of these requirements in a sustainable and cost-effective manner is extremely limiting to the potential development of commercial biofuel production under current commercial cultivation practices. Optimal sites for commercial-scale algal biofuel production would have either the required resources in close proximity or mechanisms in place to ensure adequate and uninterrupted supplies of these resources.

Innovations that result in reduced resource use along the entire algal biofuel supply chain will remove some of the existing barriers to the development of large-scale, sustainable, and economically viable algal biofuel enterprises. Therefore, a method of cultivation and harvesting algae biomass and aquaculture that embraces and mitigates concerns for large scale implementation is needed. The present invention relates to the algal (aquaculture) production supply chain and systems and methods pertaining to cultivation and harvesting.

SUMMARY OF THE INVENTION

Without being bound by any particular theory, it is believed that, if algal production is scaled up to industrial capacity, less than 6 million hectares would be needed worldwide to meet the current fuel demand. In addition, the tropical ocean alone represents approximately 6 billion hectares (60,000,000 square km) of available space for aquaculture and algae production. Accordingly, the systems and methods of the present invention use only about 0.1 percent of available tropical ocean surface area to meet global fuel requirements. In addition, the proposed system may prove commercially viable on large freshwater lakes as well further increasing the available surface area and regional access provided by the present invention.

Accordingly, the present invention relates to utilization of deep ocean water and nutrient rich fresh water from deep lakes in the cultivation and harvesting of nutrients and $CO_2$ for algae and/or other valuable aquaculture species for the production of algal biomass and the like. In particular, one embodiment of the present invention is directed to a system for cultivation and harvesting of an aquaculture product including a floating barge including a pipe and a pump, wherein the pipe extends at least about 200 meters into a body of water, and wherein the pipe and pump are capable of extracting water from the body of water at a depth of at least about 200 meters; a containment device including a plurality of open individual containers, wherein the containment device is capable of residing on the surface of the body of water, and wherein the containment device is an open system that allows the extracted water to flow through a first end to a second end; and a storage or pumping device for harvesting the aquaculture product retrieved from the second end.

In a second embodiment, the present invention is directed to a system for cultivation and harvesting of an aquaculture product including a floating barge including a pipe and a pump, wherein the pipe extends at least about 200 meters into the ocean; a containment device including a plurality of closed individual containers, wherein the containment device is capable of residing on the surface of the ocean; a towing device for the containment device; and a storage or pumping device for harvesting the aquaculture product. In this aspect of the present invention, the containment device may be a reticulated plastic photo-bioreactor. In one embodiment, the photo-bioreactor is in the form of a plastic bag or tube having a transparency of 100 percent.

The present invention is also directed to a method for the production of an algal product, including the steps of extracting water from the ocean at a depth of at least about 200 meters; pumping the extracted water into a growth medium, wherein the growth medium includes a transparent containment device capable of residing on the surface of the ocean; harvesting the resulting algal product; and drying the algal product. In this aspect of the present invention, the step of drying may further include exposing the algal product to the sun for a predetermined time.

The systems and methods of the present invention described herein provide a multitude of benefits to the future algal biofuels and aquaculture industry. For example, the systems and methods of the present invention minimize and essentially eliminate the need for land usage, which is one of the primary sustainability issues raised against algae biofuels. Cultivation in the open ocean or in large lakes is the only means of garnering enough acreage to significantly address replacement of contemporary fossil fuels with sustainable biofuels. This ensures non-competition for farm lands, agricultural crops, and water and provides inexpensive acreage for product growth and cultivation In addition, the ease of location and customization of the present invention along nearly any coast allows for not only access to more than enough free space for feedstock cultivation, but also allows for energy security for all countries on the coast with access to the ocean or seas. Although the immediate applications will be in the tropical ocean to maximize sun exposure and, hence, photosynthetic productivity, nearly all areas of the world with access to suitable water supplies, such as deep fresh water lakes or oceans, could benefit from the present invention by varying the microalgae strain cultivated to accommodate local environmental conditions.

In addition, the present invention offers numerous benefits to the environment. For example, the present invention provides a nutrient and $CO_2$ rich growing medium without fertilizers and pathogens, and without leaching the limited nutrient resources from agriculture. The methods and systems of the present invention in the open ocean application allow for the pure cultivation of the desired species without competition from more aggressive and resilient cultures and solve another of the marine algae issues raised for global sustainability. Additionally, when compared to NASA's concept (known as OMEGA), which requires attachment to shore, limits the area of applicability, exposes the system to highest energy region of ocean, the systems and the methods of the present invention are full of benefits. In fact, without the nutrient and $CO_2$ upwelling of the present invention, the surface of the open ocean is essentially a "desert" for biological productivity because it lacks nutrient resources. This "desert" actually ensures the mitigation of environmental impacts potentially created by inadvertent discharge of product algae or aquaculture into the natural system since the algae or bio-product will not survive in the natural system without the nutrient source which can easily be discontinued in the event of bag rupture or pipeline damage.

The systems and methods of the present invention also minimize or eliminate conventional harvesting issues associated with microalgae in marine designs because the resultant algal product may be contained in the containment device itself at delivery or possibly pumped to a drying/extraction site as a slurry to reduce harvesting costs typically associated with microalgae. Additionally, the present invention provides efficiencies in drying and treatment of the algal product by accessing the enormous space available at sea and extreme sun exposure in tropical locations. The systems and methods of the invention may greatly reduce the associated costs and logistic issues typically associated with three of the primary steps of algal biofuel production by drying the algal feedstock prior to mechanical or chemical extraction using solar drying technology options.

The present invention also offers significant energy savings through cultivation in the open ocean in the containment devices or open ponds. In more traditional methods, additional energy is required to either enhance the photo-availability to optimize algal growth, or, as in Hawaii, additional energy must be added to agitate the growth ponds to optimize photo-exposure and increase algal growth productivity. Neither of these additional energy requirements will be required when using the systems and methods of the present invention as the containment devices will provide optimal exposure to sunlight and the natural wave energy of the ocean or lake will provide the agitation energy required. The only energy requirements envisioned for the systems and methods of the present invention is the minimal energy required to pump the deep water to the surface, which is very minimal since there is only a need to pump against a pipe frictional head, density head difference between deep water and surface, and the elevation above sea level at photo-reactors injection point (which should be at, below, or very near the surface of the ocean), and transportation of feedstock product to shore-based extraction location. Accordingly, the systems and methods of the present invention are believed to greatly reduce current estimates for Energy Return on Investment (ERI) associated with the cultivation, harvesting, and possibly the biomass drying process.

BRIEF DESCRIPTION OF THE DRAWINGS

Further features and advantages of the invention can be ascertained from the following detailed description that is provided in connection with the drawing(s) described below.

DETAILED DESCRIPTION OF THE PRESENT INVENTION

As discussed briefly above, the present invention is directed to the utilization of deep ocean water and nutrient rich fresh water in the cultivation and harvesting of nutrients and $CO_2$ for algae and other aquaculture species for the production of algal biomass and the like.

The estimated consumptive use of fresh water for producing 1 liter of gasoline equivalent of algal biofuel is 3.15 liters to 3,650 liters, depending on (a) whether the algae or cyanobacteria need to be harvested to be processed to fuels or if they secrete fuel products; (b) whether fresh water, inland saline water, marine water, or wastewater is used as a culture medium; (c) the climatic condition of the region if open ponds are used; and (d) whether the harvest water from algae cultivation is recycled. In other words, at least 123 billion liters of water would be needed to produce 39 billion liters of algal biofuels or an equivalent of five percent of U.S. demand for transportation fuels. The estimated requirement for nitrogen and phosphorus needed to produce that amount of algal biofuels ranges from 6 million to 15 million metric tons of nitrogen and from 1 million to 2 million metric tons of phosphorus if the nutrients are not recycled or included and used in co-products. Those estimated requirements represent 44 to 107 percent and 20 to 51 percent of total nitrogen and phosphorus use in the United States, respectively.

Figure 1:
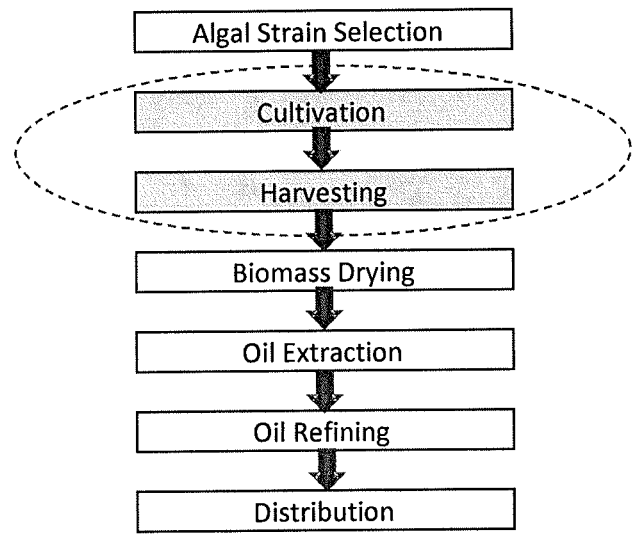
FIGS. 1 and 2 illustrate the flow process of the production of algal biofuel and general aquaculture as applicable with respect to the present invention.
Figure 2:
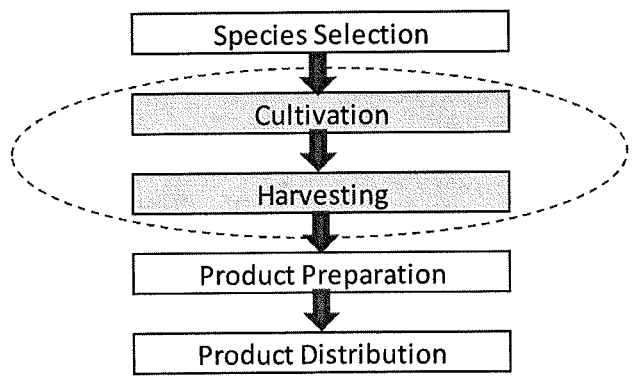

Accordingly, the present invention contemplates systems and methods for cultivating these nutrients and $CO_2$ from the deep ocean and harvesting algae biomass and other aquaculture therefrom. In addition, the present invention contemplates improved methods for drying algae biomass and further downstream applications/uses of the algae biomass. As shown in FIGS. 1 and 2, the present invention deals with a plurality of the steps in the production of algae biofuel and/or aquaculture (or algae mariculture) in general.

Figure 3:
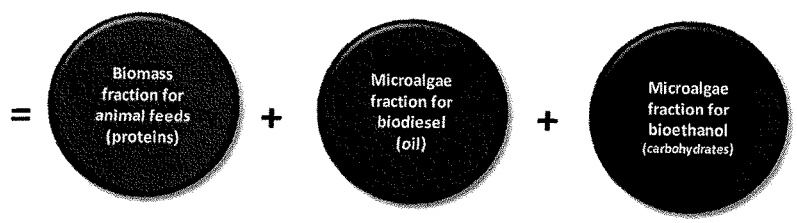
FIG. 3 illustrates the potential uses of microalgae biomass according to the present invention.

For example, as shown in FIG. 3, the microalgae biomass cultivated and harvested using the systems and methods of the present invention may be used in a plurality of ways from the direct use of whole cells as sustainable biofuel raw material, to the applications of each biomass component, e.g., protein for feed, lipids for biodiesel, pigments and polysaccharides for pharmaceutical applications. In essence, the biomass that is not used for biofuel production may be processed into many other products including, but not limited to, foods, chemicals, medicines, vaccines, minerals, animal feed, fertilizers, pigments, salad dressings, ice cream, puddings, laxatives and skin creams.

In one embodiment, the sustainable biofuel raw material that may be processed as a direct and/or indirect result of the present invention includes, but is not limited to, biodiesel, bioethanol, bio-oil, biogas, biohydrogen, and bioelectricity. In another embodiment, the protein part of algae may be extracted and used as staple food. In yet another embodiment, algal oils, pigments, and other bioactive compounds may be used as health foods, nutraceuticals or pharmaceuticals, or other renewable inputs for the food industry including as feed for livestock and aquaculture. In addition, non-food compounds can be extracted for use by the chemical industry, in cosmetics and skin care products, as organic fertilizers and as an alternative fiber source for the paper industry.

Cultivation

Figure 4:
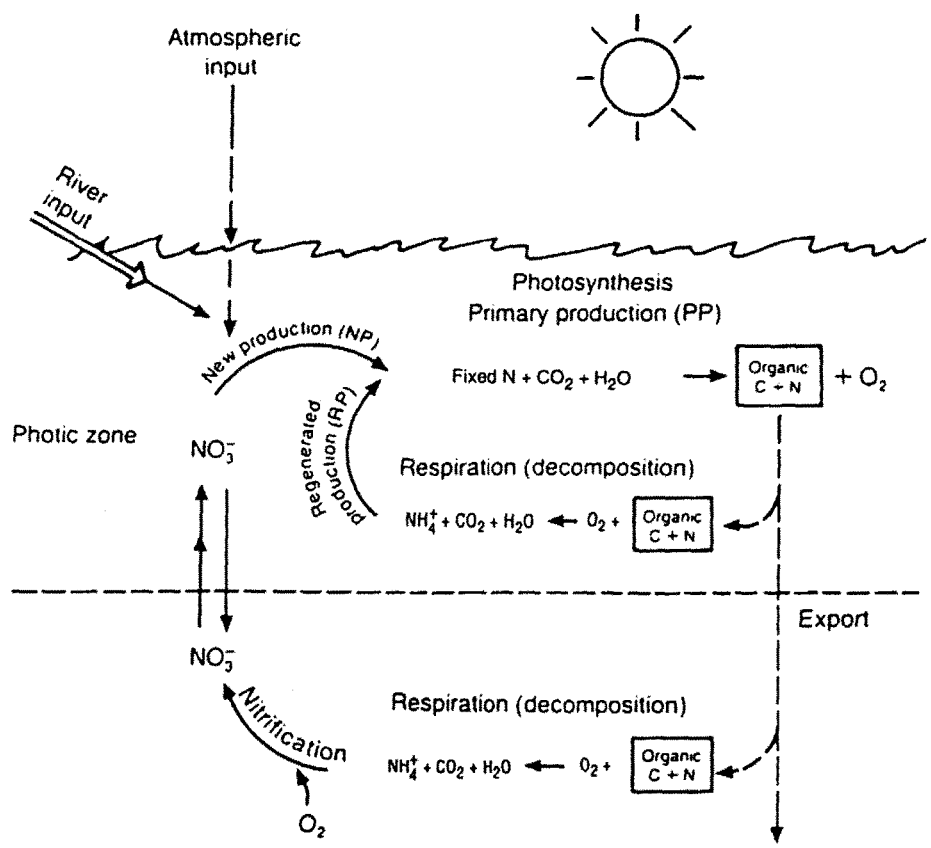
FIGS. 4 and 5 illustrate the nutrients and $CO_2$ regenerated in the deep ocean.
Figure 5:
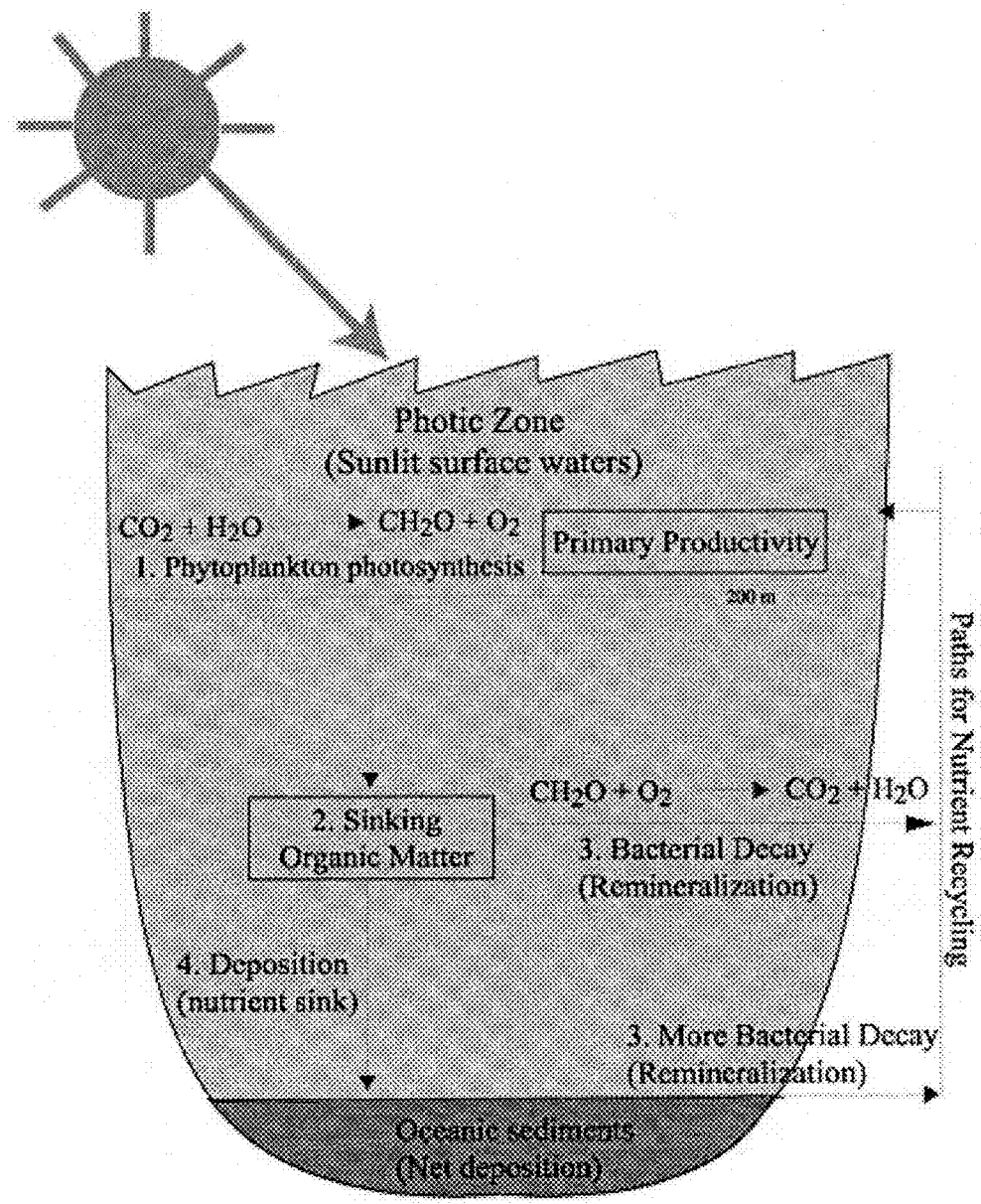
Figure 6:
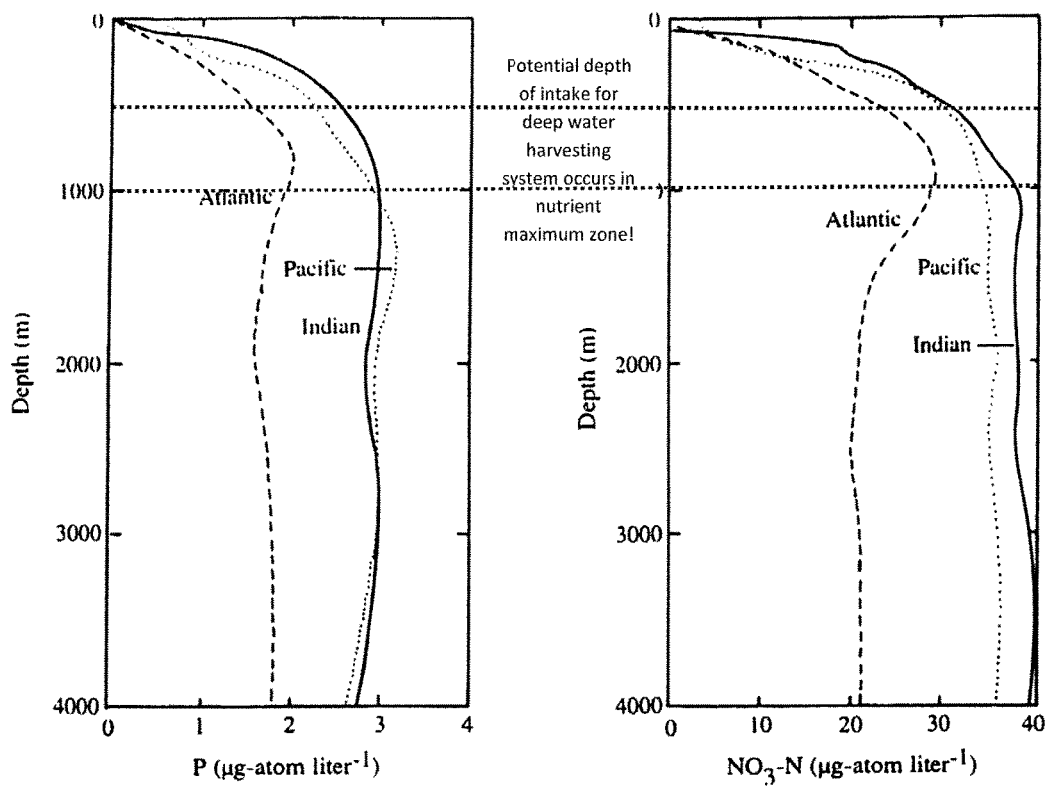
FIGS. 6 and 7 illustrate the maximum nutrient zone in accordance with the present invention.
Figure 7:
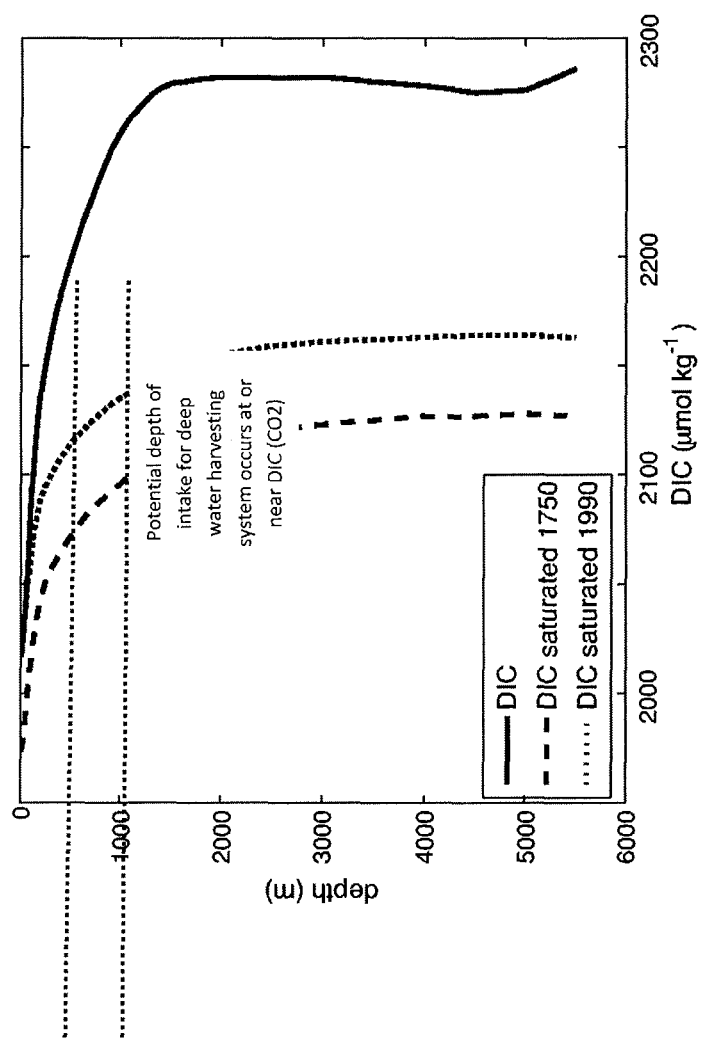

As briefly discussed above, one aspect of the present invention is the cultivation of the algae, aquaculture, and combinations thereof. As understood by those of ordinary skill in the art, regions of natural upwelling of deep ocean water are the most productive areas of ocean biology in the oceans. In particular, as illustrated in FIGS. 4-5, nutrients and $CO_2$ are regenerated in the deep ocean via microbial respiration reactions; therefore, their concentrations are much higher than at the ocean surface (orders of magnitude greater). As shown in FIGS. 6-7, the cultivation of nutrients and $CO_2$ in the present invention occurs in this nutrient maximum zone. In one embodiment, the nutrient maximum zone is at an ocean depth of at least about 200 meters. In another embodiment, the nutrient maximum zone is at an ocean depth of about 200 meters to about 1200 meters. In yet another embodiment, the nutrient maximum zone is at an ocean depth of about 500 meters to about 1000 meters.

Although the nutrient maximum zone has been described in relation to the ocean, the present invention contemplates the use of other bodies of water for the cultivation of nutrients and $CO_2$. For example, in one embodiment, the present invention utilizes nutrient rich water from deep fresh water lakes. Fresh water lakes suitable for the present invention include, but are not limited to, the Great Lakes, i.e., Lake Erie, Lake Huron, Lake Michigan, Lake Ontario, and Lake Superior.

The upwelling of the nutrients and $CO_2$ from the nutrient maximum zone may be performed in a number of suitable ways. For example, in one embodiment, the upwelling may occur using the method of sea water extraction disclosed in U.S. Pat. No. 7,658,843, the entire disclosure of which is incorporated by reference herein. Thus, in one embodiment, the upwelling may occur using a sea water pump that pumps the sea water into a flexible pipe or riser, where it is transferred to the growth vessel.

In another embodiment, the system of the invention includes a floating barge, ship, platform, buoy, or the like that houses a winch for deployment and retrieval of a deep water hose or pipe and, optionally, a pump. Once the pipe and, optionally, the pump, has been deployed to the desired depth, the pump is operated to pump sea water into the growth vessel. In another embodiment, the floating barge includes a pump and a pipe/hose that is fixed to the surface of the barge but extends to the nutrient maximum zone with a rigid pipe and surface pump.

Once brought to the surface, the deep sea water is transferred to a growth medium, or a growth vessel, to supply the nutrients and $CO_2$ to the aquaculture. The growth vessel, described in more detail below, may reside on the surface of the ocean or lake in proximity to the floating barge or platform. For example, the growth vessel may be free to float on the surface of the ocean or lake. In this instance, the growth vessel may be serviced by a mobile unit providing the growth medium and aquaculture. In another embodiment, the growth vessel is operatively connected to, at least in part, a ship, barge, buoy, or the like. In one embodiment, the growth vessel is contemplated to be a containment device that is resistant to the open ocean surface wave activity.

The containment device is not limited to a specific form and may include a plurality of individual containers that are connected in a suitable manner. For example, the containment device may include one or more individual containers in the form of bags, tubes, bladders, pods, reticulated transparent plastic photobioreactors, and/or combinations thereof. In one embodiment, the containment device includes one or more individual containers that are flexible. In another embodiment, the containment device is formed from a synthetic or semi-synthetic organic plastic material. Suitable plastic materials include, but are not limited to, polyethylene terephthalate, polyethylene, high-density polyethylene, polyvinyl chloride, polyvinylidene chloride, polypropylene, and combinations thereof. In yet another embodiment, the containment device is formed from a biopolymer. By the term, "biopolymer" as used herein, it is a meant a polymer at least partially produced from a biomass. Suitable biopolymers include, but are not limited to, cellulose, polylactic acid, naturally occurring zein, poly-3-hydroxybutyrate, and combinations thereof. The containment device may be flexible or rigid as the system and local conditions dictate for survivability and ease of cultivation and harvesting.

In one embodiment, the containment device of the present invention may include an internal gas-permeable membrane. The gas-permeable membrane allows for a constant supply of $CO_2$. In another embodiment, the containment device may include a forward osmosis membrane by utilizing a forward osmosis bag or tube. The forward osmosis membrane concentrates nutrients to stimulate growth and dewaters the algae to facilitate harvesting and drying.

The individual containers that comprise the containment device preferably provide substantial exposure to sunlight. Accordingly, the individual containers that comprise the containment device may be at least about 50 percent transparent. In another embodiment, the individual containers that comprise the containment device are at least about 60 percent transparent. In yet another embodiment, the individual containers that comprise the containment device are at least about 70 percent transparent. In still another embodiment, the individual containers that comprise the containment device are at least about 80 percent transparent. In one embodiment, the individual containers that comprise the containment device may be at least about 90 percent transparent. And, in another embodiment, the containment device is 100 percent transparent.

The ability to be flexible in the design of the containment device and the overall cultivation system allows the system to be tailored to the aquaculture species and/or desired products. In this aspect, the containment device may be designed as a photo-bioreactor where water flows through the individual containers in a way that is similar to a plug reactor in the chemical industry such that the resultant product is accumulated at the end of the reactor. The photo-bioreactors of the present invention are capable of providing water, nutrients, air, and $CO_2$ for algal production. In one embodiment, the photo-bioreactors of the present invention are in the form of flexible plastic bags or tubes having 100 percent exposure to sunlight. The bags or tubes of the photo-bioreactor may be oriented vertically or horizontally.

The containment device for certain aquaculture species may also be an open or semi-open system designed to take advantage of the atmospheric exchange and solar radiation with consistent exposure. In this aspect, the containment device provides at least one opening for exposure to the sun and atmosphere. In another embodiment, the containment device is a closed system where the growth occurs in a closed containment device. Algal "ponds" will likely be closed systems or photo-bioreactors with transparencies on all sides to encourage photosynthetic activity and aid in harvesting product algae.

The growth vessel or containment device may include a solar prewarming device for optimal growth conditions. As it will be readily apparent to one of ordinary skill in the art, growth conditions may need to be adjusted depending upon customized species requirements and local environmental conditions in order to achieve optimization.

Harvesting

Upon completion of the growth of the aquaculture, the resulting aquaculture product may be harvested. In one embodiment, if the containment device is a closed system, harvesting of the resultant product may include towing of the containment device, or specific individual containers of the containment device, to a shoreline transfer system, opening the containment device, and removing the algal product. If the containment device is a photo-bioreactor, harvesting of the resultant algal product may include detaching the bags or tubes and towing or pumping the resultant product to a shore transfer system.

In another embodiment, harvesting may include pumping the product from an open or closed system containment device into storage containers located in the proximity of the containment device. In yet another embodiment, harvesting may include pumping the product directly to shore-based drying/extraction facilities from the containment device if the containment device is located near coastal regions. If the storage containers are on barges or ships, the storage containers may then be towed and unloaded at shore or can be pumped directly to shore via a product pipeline. This may be desirable for large-scale microalgae production.

In another embodiment, the harvesting of the algal product may be transferred to a transport vessel for distribution to shore-based drying and extraction activities. In another embodiment, the transport vessel may be designed to perform the harvesting, drying, and extraction on-board and store the resultant desired product biofuel and ancillary products for distribution to refinery or processing plants directly. This may be desirable in regions far from shore, for example, in the equatorial waters where access to shore-based systems would be cost prohibitive.

Drying

The systems and methods of the present invention also contemplate enhancements and/or improvements to the biomass drying process (generally shown in FIGS. 1 and 2). For example, in one embodiment, the systems and methods of the present invention incorporate forward osmosis bags or tubes. The forward osmosis bags of the present invention allow for the natural diffusion of water through a semi-permeable membrane while blocking larger molecules such as the algae, nutrients, and pollutants. The forward osmosis bags are advantageous in that the forward osmosis membranes dewater the algae in preparation for the refining and distribution steps and clean the water released back into the surrounding seawater. In addition, the systems and methods of the present invention incorporate a pre-treatment process in the drying stage. In particular, the present invention contemplates a predetermined time for offshore drying via sun exposure prior to or in lieu of traditional mechanical drying processes. In another embodiment, the resulting algal product can be filtered from the growth medium and dried in drying containers or in ship-based drying systems. In yet another embodiment, the biomass product may be transported as a slurry/wet product to drying facilities on land via storage barges or pumped as slurry to shore-based drying facilities.

In addition, the systems and methods of the present invention contemplate the potential of exploiting the considerable available surface area of the ocean or lake and the use of solar radiation as a low-cost medium by providing a drying process where the resultant algal product is placed in a containment device, similar to the containment device described above in the cultivation stage, which allows for the evaporation of the water content while maintaining a boundary from the ocean waters upon which it floats. Such drying mechanisms are contemplated with this invention to maximize available sunlight and surface area while limiting energy requirements and system costs.

Implementation

Figure 8:
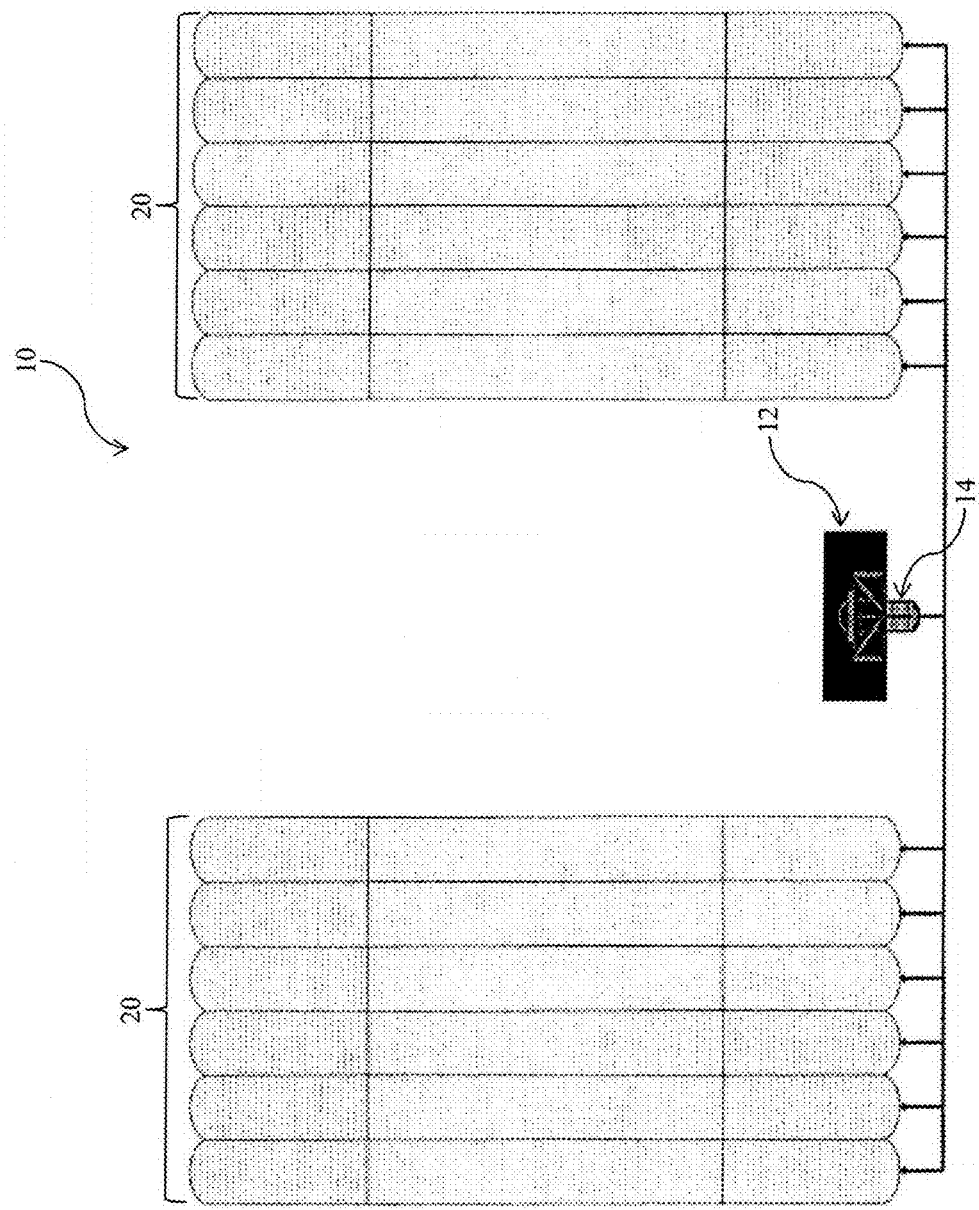
FIGS. 8 and 9 illustrate plan and side views of an offshore aquaculture farm according to one embodiment of the present invention.
Figure 9:
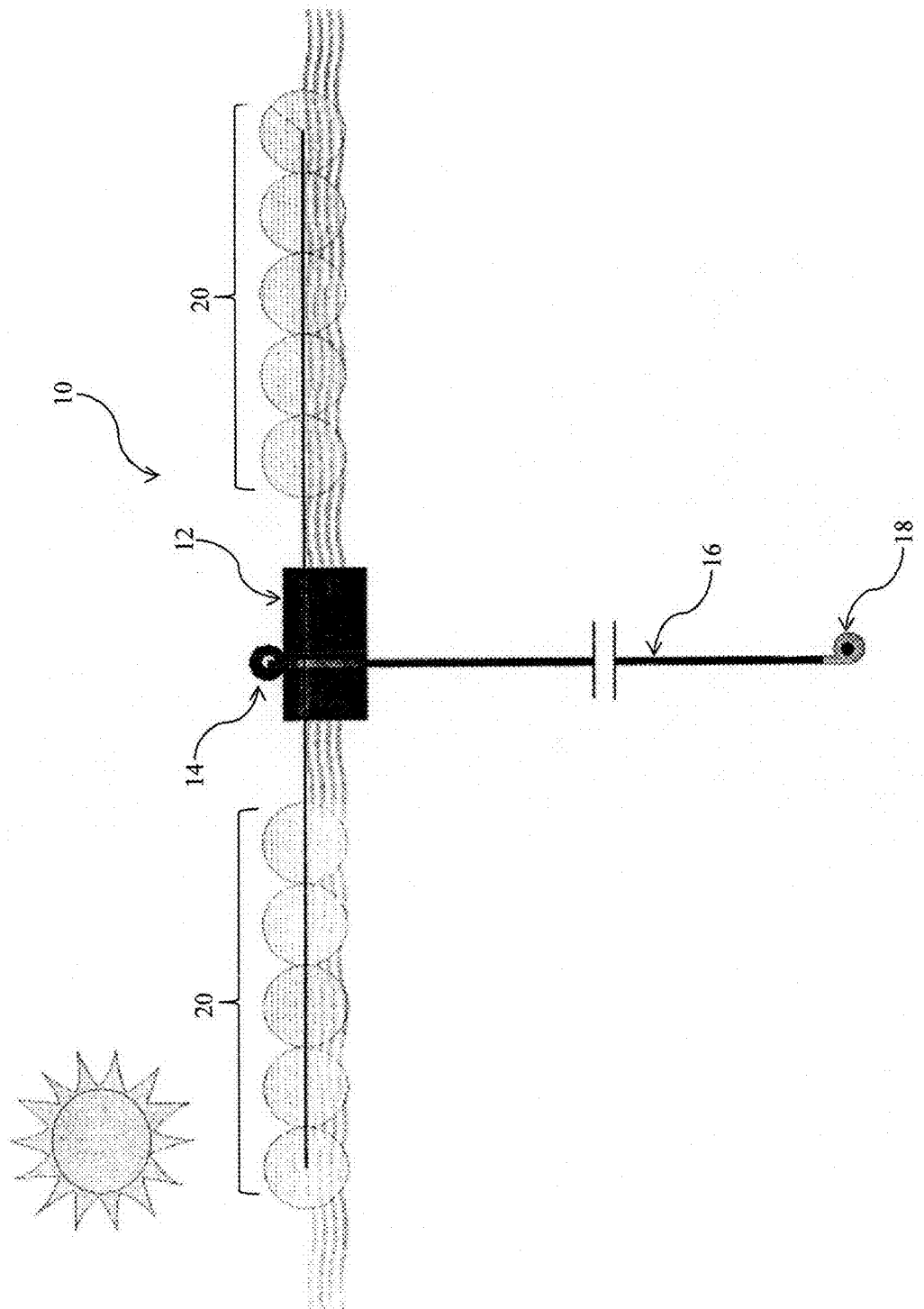
Figure 10:
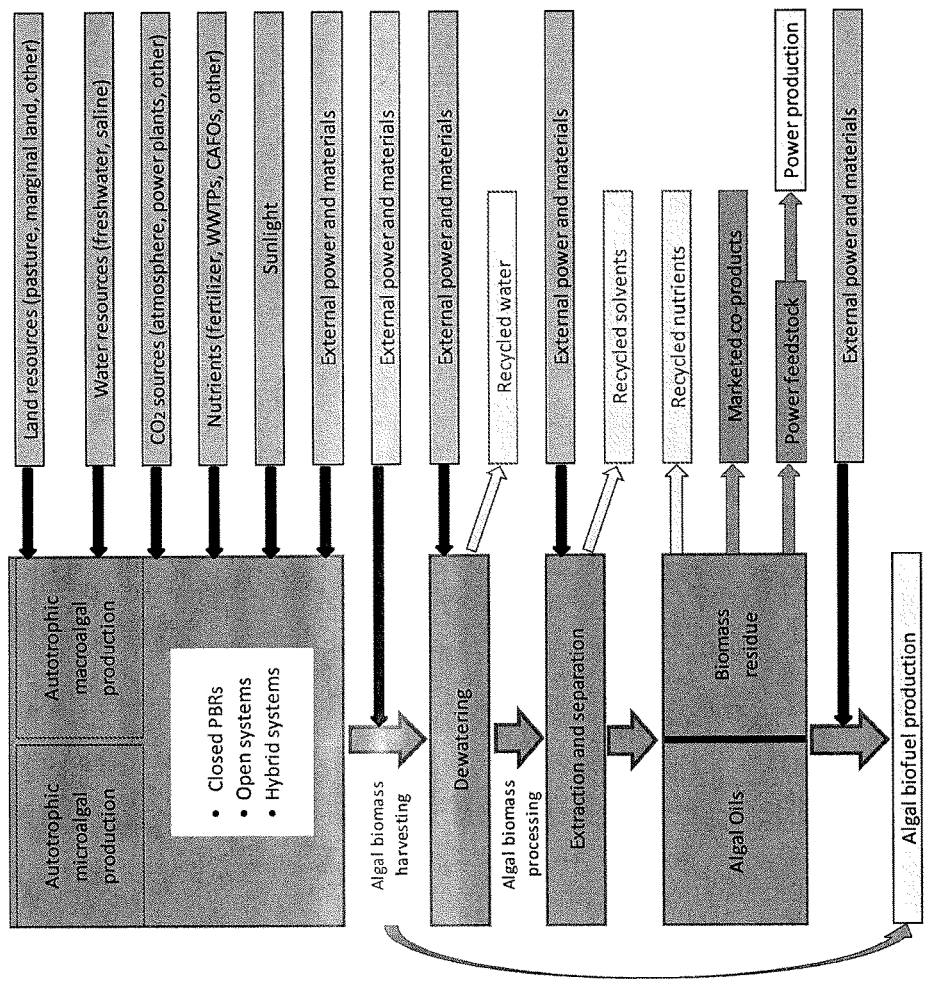
FIG. 10 illustrates the resource requirements of algae biodiesel production.

The systems and methods of the invention are contemplated to essentially turn large sea surface areas into open ocean "bio-farms", thus producing some form of high value aquaculture product. Examples of high value aquaculture product include, but are not limited to, algae for biofuel production, shrimp brood stock, and finfish for consumption. These "bio-farms" will be supported with resources/growing waters from the deep ocean (likely in excess of 500 meters depth to maximize nutrient and $CO_2$ levels for optimal growth). As shown in FIGS. 8 and 9, the bio-farm 10 may include a floating deep water harvesting barge 12 that includes a winch 14 for deployment and retrieval of the hose 16 and pump 18, the containment device 20, and a device for solar prewarming (not shown). The containment device may be a closed system, an open system, or a photo-bioreactor. In an exemplary embodiment of the present invention, the "bio-farm" produces algal biodiesel. FIG. 10 illustrates the resource requirements for a "bio-farm" in the production of algal biodiesel.

The system may be located in a variety of geographical areas. Suitable locations include, but are not limited to, oceans and large bodied lakes in temporal, sub-tropical, and tropical regions. Without being bound by any particular theory, it is believed that locating the system of the invention in an equatorial area may limit exposure to disruptive weather and sea conditions. For example, +/−5° North and South Latitude represents areas of very low storm exposure. In another embodiment, the system may be designed in a manner to allow transport or movement to protect from predicted storm activity. In another embodiment, the system may be designed with a fixed, stationary location with rigid pipe and pumping system located at the surface providing the necessary resource water to the "bio-farm" through a suitable manifold delivery system.

While the disclosure is focused mostly on the use of the present invention in the cultivation and harvesting of algae and aquaculture for biofuel production, other end uses of the present invention, including commercial applications, are contemplated. For example, if algae culture systems can be designed for small, medium and large scale production, many communities and villages throughout the world could produce their food and fuel locally on non-cropland in coastal, offshore "bio-farms." This type of integrated approach to algae biomass production and utilization of the entire product provides an unparalleled opportunity to maximize systematic efficiencies, profits, and investor returns.

In addition, the systems of the invention are contemplated for use in conjunction with coastal and offshore Ocean Thermal Energy Conversion (OTEC) and Seawater Air Conditioning (SWAC) systems. In particular, the deep ocean cooling water used in SWAC or used in the power cycle of the OTEC systems may be fed to the containment device (before and/or after usage by the OTEC system) prior to the resource return to the ocean environment.

In addition, the systems of the invention are contemplated for use in conjunction with aquaculture of feedstock and other commercially attractive species, for example, shrimp and finfish. Suitable containment systems can be developed to support such feedstock applications and support large-scale commercial fisheries and new food/commercial sources utilizing the open-ocean space and deep ocean nutrients in the area of cultivation and harvesting of important commercial feedstock species. The systems and methods of the present invention may also be developed to support offshore aquaculture/mariculture applications.

The invention described and claimed herein is not to be limited in scope by the specific embodiments herein disclosed, since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The invention claimed is:

1. A method for offshore production of an algal product, consisting of the steps of:
providing a floating barge comprising a winch operable to deploy and retrieve a pipe and a pump, wherein the pipe extends at least about 200 meters into the ocean, and wherein the pipe and pump are operable to extract seawater from the ocean at a depth of at least about 200 meters;
providing a photobioreactor operatively connected to the pipe, wherein the photobioreactor resides on the surface of the ocean;
extracting seawater from the ocean at a depth of at least about 200 meters, wherein the extracted seawater comprises a concentration of nutrients and carbon dioxide;
pumping the extracted seawater into the photobioreactor, wherein the contents of the photobioreactor consist of the extracted seawater;
growing the algal product in the photobioreactor;
transferring the algal product from the photobioreactor to an offshore transport vessel, wherein the offshore transport vessel does not have any structural connection to land, and where, aboard the offshore transport vessel, the following steps occur:
drying the algal product;
extracting from the algal product at least one ancillary product selected from the group consisting of protein, algal oil, lipids, pigments, and polysaccharides; and
storing the algal product and the at least one ancillary product.

2. The method of claim 1, wherein the step of extracting water from the ocean at a depth of about 500 meters to about 1000 meters.

3. The method of claim 1, wherein the photobioreactor is in the form of a plastic bag or tube having a transparency of 100 percent.

4. The method of claim 1, wherein the step of extracting water comprises extracting water at a depth of about 200 meters to about 1200 meters into the ocean.

5. A method for offshore production of an algal product, consisting of the steps of:
providing a floating barge comprising a winch operable to deploy and retrieve a pipe and a pump, wherein the pipe extends at least about 200 meters into the ocean, and wherein the pipe and pump are operable to extract seawater from the ocean at a depth of at least about 200 meters;
providing a photobioreactor operatively connected to the pipe, wherein the photobioreactor resides on the surface of the ocean;
growing the algal product in the photobioreactor, consisting of the steps of:
extracting seawater from the ocean at a depth of at least about 200 meters;
pumping the extracted seawater into the photobioreactor; and
harvesting the algal product.

6. The method of claim 5, wherein the step of extracting seawater comprises extracting seawater at a depth of about 200 meters to about 1200 meters into the ocean.

7. The method of claim 5, wherein the step of extracting seawater comprises extracting seawater at a depth of about 500 meters to about 1000 meters into the ocean.

8. The method of claim 5, wherein the photobioreactor is in the form of a plastic bag or tube having a transparency of 100 percent.

9. A method for offshore production of an algal product, consisting of the steps of:
- providing a floating barge comprising a winch operable to deploy and retrieve a pipe and a pump, wherein the pipe extends at least about 200 meters into the ocean, and wherein the pipe and pump are operable to extract seawater from the ocean at a depth of at least about 200 meters;
- providing a photobioreactor operatively connected to the pipe, wherein the photobioreactor resides on the surface of the ocean;
- extracting seawater from the ocean at a depth of at least about 200 meters, wherein the extracted seawater comprises a concentration of nutrients and carbon dioxide;
- pumping the extracted seawater into the photobioreactor;
- allowing the algal product to grow in the photobioreactor without external nutrients and carbon dioxide;
- transferring the algal product from the photobioreactor to an offshore transport vessel, wherein the offshore transport vessel does not have any structural connection to land, and where, aboard the offshore transport vessel, the following step occurs:
  - drying the algal product.

10. The method of claim 9, wherein the step of drying further comprises exposing the algal product to the sun for a predetermined time.

11. The method of claim 9, wherein the step of extracting seawater comprises extracting seawater at a depth of about 200 meters to about 1200 meters into the ocean.

12. The method of claim 9, wherein the photobioreactor is in the form of a plastic bag or tube having a transparency of 100 percent.

* * * * *